United States Defensive Publication [19] (H) [11] T101,305

Epstein et al. [43] Dec. 1, 1981

[54] 3[(3-ALKYLAMINO-2-HYDROXYPROPOXY)PHENYL]-1,2-PROPANEDIOLS

[76] Inventors: Joseph W. Epstein, 19 Briarwood Ave., Monroe, N.Y. 10950; Leon Goldman, 126 Grandview Ave., Nanuet, N.Y. 10954; James D. Warren, 40 W. Nauraushaun Ave., Pearl River, N.Y. 10965

[21] Appl. No.: 182,280

[22] Filed: Aug. 28, 1980

Related U.S. Application Data

[63] Continuation of Ser. No. 90,966, Nov. 5, 1979, abandoned.

[51] Int. Cl.[3] ..... C07C 93/06

[52] U.S. Cl. ..... 564/349; 260/348.15; 260/348.29; 260/348.63; 260/456 P; 260/459 R; 424/316; 424/330; 560/110; 560/142; 560/250; 568/630

[57] ABSTRACT

This invention concerns novel 3-[(3-alkylamino-2-hydroxypropoxy)phenyl]-1,2-propanediols of the formula:

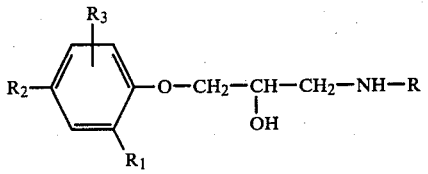

wherein R is selected from the group consisting of straight or branched-chain lower alkyls ($C_1$–$C_6$) and cycloalkyls ($C_1$–$C_6$); $R_1$ and $R_2$ are selected from the group consisting of hydrogen and 2,3-dihydroxypropyl, with the proviso that $R_1$ and $R_2$ may not be the same; and $R_3$ is selected from the group consisting of lower alkyls ($C_1$–$C_4$) and lower alkoxys ($C_1$–$C_4$); and the acid addition salts thereof. These novel compounds are useful as antiarrhythmic agents and β-andrenergic blockers in mammals.

This invention also concerns novel compounds of the formula

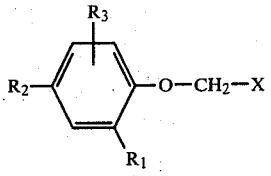

wherein $R_1$ and $R_2$ are selected from the group consisting of hydrogen and 2,3-dihydroxypropyl, with the proviso that $R_1$ and $R_2$ may not be the same; $R_3$ is selected from the group consisting of lower alkyls ($C_1$–$C_4$) and lower alkoxys ($C_1$–$C_4$); and X is selected from the group consisting of

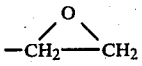

and —CHOH—$CH_2$—Z (or a mixture of these compounds wherein X has both meanings stated above) where Z may be halogen, alkoxy sulfonyl and aryloxysulfonyl; and the acid-addition salts thereof. These compounds are useful as intermediates for the preparation of the active antiarrhythmic and β-andrenergic blocking compounds described above.

This invention also concerns a process for preparing said antiarrhythmic and β-andrenergic blocking compounds from said intermediates.

8 Claims, No Sheets Drawing,

30 Pages Specification

The file of this unexamined application may be inspected and copies thereof may be purchased (849 O.G. 1221, Apr. 9, 1968).